US007648691B2

(12) United States Patent
Nagata

(10) Patent No.: US 7,648,691 B2
(45) Date of Patent: Jan. 19, 2010

(54) METHOD OF FULLERENE SEPARATION AND COMPLEX CONTAINING FULLERENE

(75) Inventor: Koichi Nagata, Kitakyushu (JP)

(73) Assignee: Frontier Carbon Corporation, Tokyo (JP)

( * ) Notice: Subject to any disclaimer, the term of this patent is extended or adjusted under 35 U.S.C. 154(b) by 461 days.

(21) Appl. No.: 10/574,805

(22) PCT Filed: Aug. 10, 2004

(86) PCT No.: PCT/JP2004/011484

§ 371 (c)(1),
(2), (4) Date: Apr. 5, 2006

(87) PCT Pub. No.: WO2005/035442

PCT Pub. Date: Apr. 21, 2005

(65) Prior Publication Data

US 2007/0134150 A1 Jun. 14, 2007

(30) Foreign Application Priority Data

Oct. 8, 2003 (JP) .............................. 2003-349911

(51) Int. Cl.
*B01J 19/08* (2006.01)
(52) U.S. Cl. .................. 423/445 B; 977/845; 977/734; 210/638; 423/461
(58) Field of Classification Search ................. 423/461, 423/460, 445 B; 210/198.2, 502.1, 635, 210/656

See application file for complete search history.

(56) References Cited

U.S. PATENT DOCUMENTS

| 5,273,729 A | 12/1993 | Howard et al. |
| 5,904,852 A * | 5/1999 | Tour et al. .................... 210/635 |
| 6,765,098 B1 * | 7/2004 | Nakamura et al. ....... 548/338.1 |

FOREIGN PATENT DOCUMENTS

| AU | 10101/95 | 7/1995 |
| EP | 0 662 449 | 7/1995 |
| EP | 0662449 A1 | 7/1995 |
| EP | 0662449 B1 | 7/1995 |
| JP | 6-507879 A | 9/1994 |
| JP | 7-237911 | 9/1995 |

(Continued)

OTHER PUBLICATIONS

Konarev et al, Molecular Complexes, J Solid State Chem, 168, 2002, 474-485.*

(Continued)

*Primary Examiner*—Melvin C Mayes
*Assistant Examiner*—Bijay S Saha
(74) *Attorney, Agent, or Firm*—Westerman, Hattori, Daniels & Adrian, LLP

(57) ABSTRACT

A fullerene mixture comprising any two or more of C60, C70 and higher fullerenes having greater than 70 carbon atoms is brought into contact with an amine having two or more nitrogen atoms, especially an amine having an amidine structure, in a solvent to form a complex of a specific fullerene contained in the fullerene mixture and the amine, and the complex is separated from a solution in which fullerenes not forming the complex are dissolved. Consequently, a method of fullerene separation, by which the specific fullerene is separated from the fullerene mixture with ease and at low cost, and the complex having the fullerene can be provided.

16 Claims, 1 Drawing Sheet

FOREIGN PATENT DOCUMENTS

| | | |
|---|---|---|
| JP | 2654918 B2 | 9/1997 |
| JP | 2802324 B2 | 9/1998 |
| JP | 11-240705 A | 9/1999 |
| JP | 2002-234717 | 8/2002 |
| WO | 92/04279 A1 | 3/1992 |
| WO | WO/02/079142 * | 10/2002 |

OTHER PUBLICATIONS

Bhasikuttan et al, Interaction of Triplet, J Photo & Photobio, 143, 2001, 17-21.*

A. Skiebe et al.; "[DBU]$C_{60}$ Spin pairing in a fullerene salt", Chemical Physics Letters, vol. 220, Mar. 25, 1994, pp. 138-140. Cited in the ISR.

H. Klos et al.; "Doping of $C_{60}$ with tertiary amines: TDAE, DBU, DBN. A comparative study", Chemical Physics Letters, vol. 224, Jul. 15, 2994, pp. 333-337. Cited in the ISR.

K. Tanaka et al.; "Magnetic properties of TDAE-$FC_{60}$ and TDAE-$C_{70}$. A comparative study", Physics Letters A, vol. 164, 1992, pp. 221-226. Cited in the ISR.

D. K. Palit et al.; "Dynamics of charge transfer in the excited amine complexes of the fullerenes $C_{60}$ and $C_{70}$. A picosecond laser flash photolysis study"; Chemical Physics Letters, vol. 198, No. 1, 2, Oct. 2, 1992, pp. 113-117. Cited in the ISR.

D. V. Konarev et al.; "Molecular Complexes of Fullerenes $C_{60}$ and $C_{70}$ with Saturated Amines"; Journal of Solid State Chemistry, vol. 168, 2000, pp. 474-485. Cited in the ISR.

K. Nagata et al.; "Isolation of a hundred-gram quantity of higher fullerene from a fullerene mixture", 2P-02, p. 105. Cited in the ISR, Jul. 2004.

International Search Report of PCT/JP2004/011484, dated Oct. 26, 2004.

* cited by examiner

METHOD OF FULLERENE SEPARATION AND COMPLEX CONTAINING FULLERENE

TECHNICAL FIELD

The present invention relates to a method of fullerene separation and to a complex of a fullerene and an amine.

BACKGROUND ART

Fullerenes referred to as C60 and C70, carbon clusters having a closed-shell structure, have been recently proposed as new carbon materials, for example, as shown in Japanese Patent No. 2802324. Since these materials are expected to show special properties because of their unique molecular structures, research on their properties and development of use has been increasingly made, and fullerenes are expected to be used in fields of, e.g., diamond coatings, battery materials, paints, heat insulating materials, antifrictions, pharmaceuticals, and cosmetics.

As a method for producing fullerenes, a method has been proposed in which a carbon compound is burned to produce fullerenes, for example, as shown in Published Japanese Translation of PCT International Application No. H06-507879. Also, another method has been proposed in which an aromatic hydrocarbon such as benzene and an oxygen-containing gas are introduced into a reactor and subjected to incomplete combustion under reduced pressure to produce fullerenes.

Fullerene-containing soot obtained by a combustion method etc. contains a fullerene mixture having any two or more of C60, C70 and higher fullerenes having greater than 70 carbon atoms (any one or more of C76, C78, C82, C84, C90, C96, C120, etc.), and a soot residue (e.g. polycyclic aromatic hydrocarbons such as acenaphthylene, fluorene, phenanthrene, pyrene, benzo[b]fluorene, benzo[c]phenanthrene, benzo[a]anthracene, triphenylene, and/or benzopyrene, carbon having a graphite structure, hydrocarbons having a graphite structure as a skeleton, and carbonaceous polymers such as carbon black). A solvent extraction method has also been known in which the soot is brought into contact with a solvent in which the fullerenes are soluble to dissolve the fullerenes in the solvent, and the soot residue insoluble in the solvent is removed therefrom to obtain the fullerene mixture.

Moreover, as a method for separation of a specific fullerene from the fullerene mixture, a separation method using a column filled with a separating agent such as activated carbon has been known. Another method has been known in which a host compound such as a calixarene or a cyclic phenol sulfide (a calixarene having a sulfur atom) is brought into contact with a specific fullerene (a guest compound) to form an inclusion compound, thereby separating the specific fullerene from fullerenes not included in the inclusion compound (See Japanese Patent No. 2654918 and Published Japanese Patent Application No. 11-240705, for example).

DISCLOSURE OF INVENTION

However, the separation of a specific fullerene using chromatography requires a great amount of a solvent and is disadvantageous in that the fullerene that interacts strongly with the separating agent is adsorbed by the separating agent, which inhibits recovery of the fullerene. Moreover, although the separation of the specific fullerene using the host compound requires a relatively small amount of the solvent used, the calixarene used as the host compound is a highly designed compound and thus expensive, thereby increasing the cost for separation of the specific fullerene. Another disadvantage is complexity of the operation since change in solvent system is required to separate the specific fullerene and the host compound from the synthesized inclusion compound.

The present invention has been made in view of the above problems and aims to provide a method of fullerene separation by which a specific fullerene is separated from a fullerene mixture with ease and at a low cost, and to provide a complex containing a fullerene.

A first aspect of the present invention for attaining the above object provides a method of fullerene separation comprising the steps of: bringing a fullerene mixture into contact with an amine A in a solvent to form a complex of a specific fullerene contained in the fullerene mixture with the amine A, the fullerene mixture comprising any two or more of C60, C70 and higher fullerenes having greater than 70 carbon atoms, the amine A having two or more nitrogen atoms; and separating the complex from a solution in which fullerenes not forming the complex are dissolved.

In the method of fullerene separation according to the first aspect of the present invention, soot including the fullerene mixture comprising any two or more of C60, C70, and higher fullerenes having greater than 70 carbon atoms can be produced by such as: (1) an arc-discharge method in which electrodes made of a carbonaceous material such as graphite are used as starting material and arc discharge is applied between the electrodes to evaporate the material; (2) a resistance heating method in which a carbonaceous material is vaporized by application of a high current; (3) a laser vaporization method in which a carbonaceous material is vaporized by irradiation of a pulsed laser having a high energy density; or (4) a combustion method in which organic matter such as benzene is subjected to incomplete combustion.

The soot containing fullerenes produced by these methods further contains, besides the fullerenes, a polycyclic aromatic hydrocarbon such as acenaphthylene, fluorene, phenanthrene, pyrene, benzo[b]fluorene, benzo[c]phenanthrene, benzo[a]anthracene, triphenylene, and benzopyrene, carbon having a graphite structure, a hydrocarbon having a graphite structure as a skeleton, and a carbonaceous polymer such as carbon black.

Accordingly, a fullerene-enriched material prepared by partly removing graphite, carbon black, and the like from the soot is preferred as the fullerene mixture, and a fullerene-enriched material composed of only fullerenes prepared by entirely removing graphite, carbon black, and the like from the soot is more preferred. The fullerene-enriched material is obtained by concentrating fullerenes from the soot by various methods, and the methods are not particularly limited. The fullerene-enriched material includes, e.g., a fullerene sublimate obtained from the soot by a sublimation method, a fullerene-containing residue produced by evaporating to dryness a fullerene solution obtained by a solvent extraction method, a fullerene-containing solid obtained by subjecting the soot to column chromatographic separation, and a mixture thereof.

The solvent used in the method according to the first aspect of the present invention is a solvent in which fullerenes are soluble, e.g., an aromatic hydrocarbon, an aliphatic hydrocarbon and a chlorinated hydrocarbon, which may be cyclic or acyclic, and one or more of these solvents may be used in combination at any ratio.

Here, the aromatic hydrocarbon is any hydrocarbon compound having at least one benzene nucleus in a molecule, e.g., an alkylbenzene such as benzene, toluene, xylene, ethylbenzene, n-propylbenzene, isopropylbenzene, n-butylbenzene, sec-butylbenzene, tert-butylbenzene, 1,2,3-trimethylbenzene, 1,2,4-trimethylbenzene, 1,3,5-trimethylbenzene, 1,2,3,4-tetramethylbenzene, 1,2,3,5-tetramethylbenzene, diethylbenzene, and cymene; an alkylnaphthalene such as 1-methylnaphthalene and 2-methylnaphthalene; and tetralin.

The aliphatic hydrocarbon may be either cydic or acyclic. The cycloaliphatic hydrocarbon includes monocyclic aliphatic hydrocarbons such as cyclopentane, cyclohexane, cycloheptane, cyclooctane, and derivatives thereof such as methylcyclopentane, ethylcyclopentane, methylcyclohexane, ethylcyclohexane, 1,2-dimethylcyclohexane, 1,3-dimethylcyclohexane, 1,4-dimethylcyclohexane, isopropylcyclohexane, n-propylcyclohexane, tert-butylcyclohexane, n-butylcyclohexane, isobutylcyclohexane, 1,2,4-trimethylcyclohexane, and 1,3,5-trimethylcyclohexane. The cycloaliphatic hydrocarbon further includes polycyclic aliphatic hydrocarbons such as decalin, and acyclic aliphatic hydrocarbons such as n-pentane, n-hexane, n-heptane, n-octane, isooctane, n-nonane, n-decane, n-dodecane, and n-tetradecane.

Furthermore, the chlorinated hydrocarbon includes such as dichloromethane, chloroform, carbon tetrachloride, trichloroethylene, tetrachloroethylene, 1,2-dichloroethane, 1,1,2,2-tetrachloroethane, chlorobenzene, dichlorobenzene, and 1-chloronaphthalene.

As the solvent, ketone having 6 or greater carbon atoms, ester having 6 or greater carbon atoms, ether having 6 or greater carbon atoms, carbon disulfide, etc. maybe used.

Here, among these solvents, from an industrial point of view, solvents that are liquid at room temperature and have boiling points of 100 to 300° C., especially 120 to 250° C., are preferred. Specifically, for example, it is preferable to use an alkylbenzene such as toluene, xylene, mesitylene, 1-methylnaphthalene, 1,2,3,5-tetramethylbenzene, and 1,2,4-trimethylbenzene, and/or an aromatic hydrocarbon such as naphthalene derivatives of tetralin. These solvents may be used alone, or two or more of these solvents may be used in combination as a mixed solvent.

The water-soluble amine includes, for example, 2-aminopyridine, and guanidine. The amine tends to form a complex preferentially with the higher fullerenes having greater than 70 carbon atoms and stronger electron-accepting property.

The amine can be added as follows. A liquid, lipid-soluble amine can be added as it is or may be added after being diluted with a solvent. A solid, lipid-soluble amine is preferably dissolved in a solvent which is capable of dissolving the amine and miscible with a solvent in which fullerenes are dissolved. Generally, the water-soluble amine is hardly miscible with a solvent that dissolves fullerenes such as an aromatic hydrocarbon. Therefore, it is preferable that the water-soluble amine is dissolved in a polar solvent such as water so that the amine contacts with the solvent in which fullerenes are dissolved in a two-layer system.

In any method of adding the amine, it is preferable to stir a fullerene solution at a proper speed. A preferred temperature for dripping the amine is in a range of −50 to 100° C., and especially a temperature of −20 to 50° C. increases formation speed of the complex, and is thus more preferred. Amount of the amine to be dripped depends on a fullerene content to be separated, but in general, the amount is preferably 2 to 50 molar equivalents of fullerenes to be separated. After completion of the dripping, it is important to mature the fullerene solution until the complex is formed sufficiently.

Next, the formed complex is separated from the fullerene solution. The complex is generally insoluble in solvents that dissolve fullerenes. Therefore, it is preferable to use a method such as filtration or decantation for the separation. Moreover, when the formed complex is soluble in the solvent, the complex can be separated from the fullerenes not forming the complex by crystallization etc.

Accordingly, fullerenes can be recovered from the solution in which fullerenes not forming the complex are dissolved. When the solution contains an excessive amount of the amine, the amine can be removed from the solution by addition of an organic acid to precipitate the amine as a salt, or by mixing the solution with an acid aqueous solution or water to remove the amine into a water layer. In the solution from which the amine has been removed, only fullerenes not forming the complex are dissolved. The solution may be used in a subsequent reaction as it is, or the fullerenes may be extracted therefrom as a solid by solvent elimination, crystallization, sublimation or any combination of these methods.

As described above, the method according to the first aspect of the present invention allows separation of the specific fullerene and the fullerenes not forming the complex from the fullerene mixture.

A second aspect of the present invention provides a method of fullerene separation according to the first aspect of the present invention, wherein the complex is insoluble in the solvent. In this case, the complex forms a precipitate in the solvent, thus the complex can be separated from a solution in which fullerenes not forming the complex are dissolved using a method such as filtration or decantation.

A third aspect of the present invention provides a method of fullerene separation according to the first or the second aspect of the present invention, wherein the complex is dissociated into the specific fullerene and the amine A to obtain the specific fullerene. In this method, the complex is dissociated into the specific fullerene and the amine by addition of a substance having stronger interaction with the amine than with the specific fullerene, particularly an acid such as an organic acid or inorganic acid. The complex can also be dissociated into the fullerene and the amine by chromatography having a stationary phase that strongly interacts with an amine (or amines).

A fourth aspect of the present invention provides a method of fullerene separation according to the third aspect of the present invention, wherein the dissociation of the complex is carried out by bringing the complex into contact with an acid. For example, firstly the complex is suspended in a solvent capable of dissolving the fullerenes. Subsequently, while the suspension is stirred well, the acid, for example, an organic acid such as acetic acid, trifluoroacetic acid, or methanesulfonic acid, or an inorganic acid such as sulfuric acid, hydrochloric acid, or phosphoric acid is added to turn the amine into a salt with the acid, thereby separating the fullerenes and making the fullerenes to be in a solution state. By separating the salt by e.g. water washing or filtration, a solution of the specific fullerene and the salt of the amine with the acid are obtained. This solution can be used as it is for a reaction etc., or solid fullerenes can be extracted therefrom by a method such as solvent elimination, crystallization, sublimation, or any combination thereof.

By the method of the above-described first to fourth aspects of the present invention, the specific fullerene can be obtained at high purity. Moreover, repeating all of or part of the above procedures is effective for further enhancement of fullerene purity. Also, executing the method of the present invention in combination with any one or more of the techniques of chromatography, crystallization sublimation, inclusion, etc., which are conventionally used as fullerene separation methods, is also effective for enhancement of fullerene purity.

A fifth aspect of the present invention for attaining the above object provides a method of fullerene separation comprising: a first process of bringing a fullerene mixture comprising C60, C70 and higher fullerenes having greater than 70 carbon atoms into contact with an amine B having two or more nitrogen atoms in a solvent to generate a first complex formed by the higher fullerenes and the amine B; a second process of separating the first complex from a first solution in which the C60 and the C70 are dissolved; a third process of bringing the first solution into contact with an amine C having two or more nitrogen atoms to obtain a second complex formed by the C70 and the amine C; and a fourth process of separating the second complex from a second solution in which the C60 is dissolved.

In the method of fullerene separation according to the fifth aspect of the present invention, the same fullerene mixture, amine, and solvent as those used in the method of the first to fourth aspects of the invention can be used, and the method of adding the solvent can be done in the same way as in the method according to the first aspect of the invention. The formed first and the second complexes are generally insoluble in solvents that dissolve fullerenes, and hence it is preferable to use a method such as filtration or decantation for separation of these complexes. Moreover, when the formed complexes are soluble in the solvent, the complexes can be separated from the fullerenes not forming the complexes by crystallization etc.

Although the C60 can be recovered from the second solution, when the second solution contains an excessive amount of the amine, it is preferable to remove the amine. As a method for removing the amine, there are, for example, a method in which an organic acid is added to the solution to generate and precipitate a salt of the amine with the organic acid, and a method in which the solution is mixed with an acid aqueous solution or water to remove the amine into a water layer. The solution from which the amine has been removed only contains C60, and the solution can be used in a subsequent reaction as it is, or solid C60 can be extracted therefrom by a method of solvent elimination, crystallization, sublimation, or any combination of these methods.

By the fifth aspect of the present invention, C60, C70 and higher fullerenes having greater than 70 carbon atoms can be respectively separated easily at low cost.

A sixth aspect of the present invention provides a method of fullerene separation according to the fifth aspect of the present invention, wherein the first and the second complexes are insoluble in the solvent. In this case, the first and the second complexes form precipitates in the solvent, thus the complexes can be separated from a solution in which fullerenes not forming the complexes are dissolved by a method of filtration, decantation or the like.

A seventh aspect of the present invention provides a method of fullerene separation according to the fifth or the sixth aspect of the present invention, wherein the first complex is dissociated into the higher fullerenes and the amine B to obtain the higher fullerenes. In this method, a substance having stronger interaction with the amine than with the higher fullerenes, especially an acid such as an organic or inorganic acid, is added to dissociate the first complex into the higher fullerenes and the amine. The first complex may also be dissociated by chromatography having a stationary phase that strongly interacts with an amine (amines).

An eighth aspect of the present invention provides a method of fullerene separation according to the seventh aspect of the present invention, wherein the dissociation of the first complex is carried out by bringing the first complex into contact with an acid. Namely, the first complex is suspended in a solvent capable of dissolving the fullerenes. Subsequently, while the resultant solution is stirred well, the acid e.g. an organic acid such as acetic acid, trifluoroacetic acid, or methanesulfonic acid, or an inorganic acid such as sulfuric acid, hydrochloric acid, or phosphoric acid is added to form a salt of the amine and the acid, thereby making the fullerenes to be in a solution state by dissociation. By separating the salt by water washing, filtration or the like, a solution of a specific fullerene (higher fullerenes) having strong interaction with the amine can be obtained. This solution can be used as it is in a subsequent reaction, or solid fullerenes can be extracted therefrom by a method such as solvent elimination, crystallization, sublimation, or any combination of these methods.

A ninth aspect of the present invention provides a method of fullerene separation according to one of the fifth to eighth aspects of the present invention, wherein the second complex is dissociated into the C70 and the amine C to obtain the C70. Here, the second complex is dissociated into the C70 and the amine by addition of a substance having stronger interaction with the amine than with the C70, specifically an acid such as an organic acid or an inorganic acid. The second complex can also be dissociated by chromatography having a stationary phase that strongly interacts with an amine (amines).

A tenth aspect of the present invention provides a method of fullerene separation according to the ninth aspect of the present invention, wherein the dissociation of the second complex is carried out by bringing the second complex into contact with an acid. Namely, the second complex is suspended in a solvent capable of dissolving fullerenes. Subsequently, while the resultant solution is stirred well, the acid e.g. an organic acid such as acetic acid, trifluoroacetic acid, or methanesulfonic acid, or an inorganic acid such as sulfuric acid, hydrochloric acid, or phosphoric acid is added to form a salt of the amine and the acid, thereby making the fullerene to be in a solution state by dissociation. By separating the salt by water washing, filtration or the like, a solution of a specific fullerene (C70) having strong interaction with the amine can be obtained. This solution can be used as it is in a subsequent reaction, or solid fullerene can be extracted therefrom by a method such as solvent elimination, crystallization, sublimation, or any combination of these methods.

An eleventh aspect of the present invention provides a method of fullerene separation according to one of the first to fourth aspects of the present invention, wherein the amine A has a substructure in which the two nitrogen atoms are bonded through one atom. A twelfth aspect of the present invention provides a method of fullerene separation according to one of the fifth to tenth aspects of the present invention, wherein each of the amines B and C has a substructure in which the two nitrogen atoms are bonded through one atom. As the amines (i.e., the amines A, B and C), compounds having the same or different chemical compositions in which, for example, two nitrogen atoms are bonded through one atom of carbon, nitrogen or the like may be used. The amines include, for example, tetrakis(dimethylamino)ethylene and 1-alkyl-1, 2,3-triazoline. Accordingly, the amines are allowed to form complexes preferentially with fullerenes.

A thirteenth aspect of the present invention provides a method of fullerene separation according to the eleventh or twelfth aspect of the present invention, wherein each of the amines having the substructure in which the two nitrogen atoms are bonded has an amidine structure represented by a formula (1).

(1)

Here, the amines having the amidine structure include, e.g., TMG, IDN, DBU, DBN, 1,2-dimethyl-1,4,5,6-tetrahydropyrimidine, 1-methyl-2-imidazoline, 2-alkylamidine, 2-aminopyridine, and guanidine.

A fourteenth aspect of the present invention provides a method of fullerene separation according to the thirteenth aspect of the present invention, wherein each of the amines having the amidine structure has a cyclic amidine structure represented by a formula (2).

(2)

(n is an integer of 2 or more.)

In the method according to the fourteenth aspect of the invention, the amines having the cyclic amidine structure include IDN, DBU, DBN, 1,2-dimethyl-1,4,5,6-tetrahydropyrimidine, 1-methyl-2-imidazoline, and 2-aminopyridine. For example, when a complex of C60 with DBU, a complex of C70 with DBU, and a complex of a higher fullerene with DBU are formed, each of the complexes is formed by one or two coordinates of DBU and one molecule of fullerene as shown in a formula (3). (In the formula (3), "Fullerene" is a generic term to represent C60, C70 and higher fullerenes)

$$\text{Fullerene} \cdot (\text{DBU})_n \quad (3)$$

(n=1-2)

A fifteenth aspect of the present invention provides a method of fullerene separation according to the fourteenth aspect of the invention, wherein each of the amines having the cyclic amidine structure is any one of 1,8-diazabicyclo[5.4.0]undec-7-ene and 1,5-diazabicyclo[4.3.0]non-5-ene.

A sixteenth aspect of the present invention for attaining the above object provides a complex comprising a fullerene and an amine having an amidine structure. Here, the amine having the amidine structure includes, e.g., straight-chain TMG, 2-alkylamidine, and guanidine; monocyclic IDN, 1,2-dimethyl-1,4,5,6-tetrahydropyrimidine, 1-methyl-2-imidazoline, and 2-alkylamidine; and polycyclic DBU and DBN.

A seventeenth aspect of the present invention provides a complex according to the sixteenth aspect of the invention, wherein the fullerene has 70 or greater carbon atoms. The fullerene having 70 or greater carbon atoms includes C70, C76, C78, C82, C84, C86, C88, C90, C92, C94, and C96, and also includes derivatives thereof.

An eighteenth aspect of the present invention provides a complex according to the sixteenth or seventeenth aspect of the invention, wherein the amine is any one of 1,8-diazabicyclo[5.4.0]undec-7-ene and 1,5-diazabicyclo[4.3.0]non-5-ene.

Since the complex according to the sixteenth to the eighteenth aspects of the present invention includes the fullerene and the amine having the amidine structure, the complex may be used as an intermediate in the isolation of the specific fullerene.

BEST MODE FOR CARRYING OUT THE INVENTION

Figure 1:
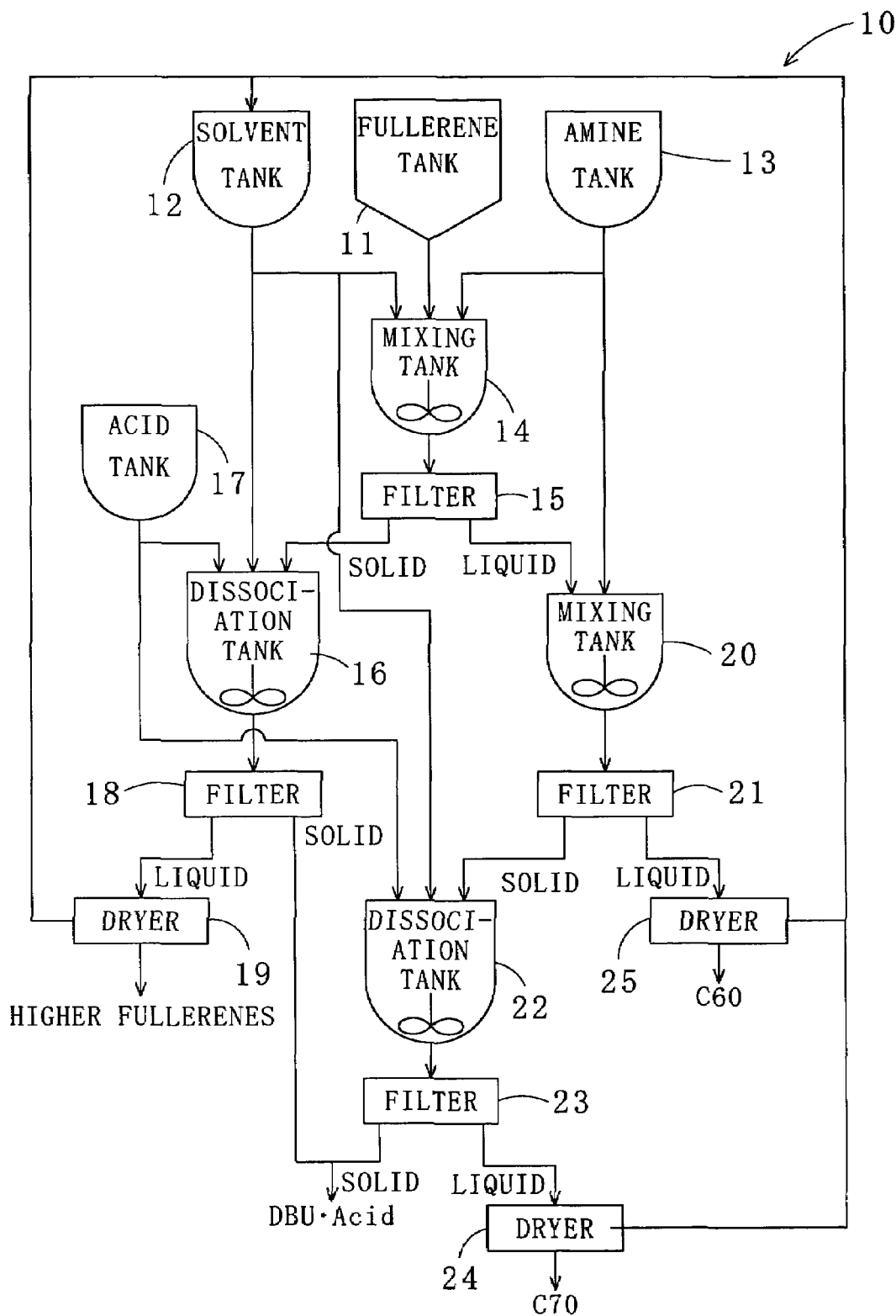
FIG. 1 is an explanatory diagram of a fullerene producing apparatus to which a method of fullerene separation according to one embodiment of the present invention is applied.

As shown in FIG. 1, a fullerene producing apparatus 10, to which a method of fullerene separation according to one embodiment of the present invention is applied, is provided to separate C60, C70 and higher fullerenes having greater than 70 carbon atoms individually from a fullerene mixture comprising the C60, the C70 and the higher fullerenes. Hereafter, the method of fullerene separation employing the fullerene producing apparatus 10 will be described in detail.

(First Process)

The fullerene producing apparatus 10 has a fullerene tank 11 for storing the fullerene mixture. As the fullerene mixture, a solid containing C60, C70 and higher fullerenes having greater than 70 carbon atoms is used. The solid is extracted by adding soot obtained by a combustion method etc. to a solvent (e.g., 1,2,4-trimethylbenzene, hereafter referred to as TMB), removing a soot residue in the soot from the solution, and further removing the solvent.

The soot used may also be produced by an arc-discharge method, a resistance heating method or a laser vaporization method instead of the combustion method, however, the combustion method is preferred because of highness of fullerene content in the soot (e.g., the soot produced by the combustion method contains 10 to 30 wt. % fullerenes). As the fullerene mixture, as described above, a fullerene-enriched material obtained by removing all of or part of graphite and carbon black etc. from the soot may also be used.

The apparatus 10 includes a solvent tank 12 for storing a solvent, e.g. TMB, that dissolves the fullerenes. The solvent used in the apparatus 10 includes, besides TMB, solvents in which the fullerenes are soluble, such as aromatic hydrocarbons, aliphatic hydrocarbons, chlorinated hydrocarbons, which may be cyclic or acyclic. These solvents may be used alone or two or more of these solvents may be used in combination at any ratio. As described before, solvents that are liquid at room temperature and have boiling points of 100 to 300° C., especially 120 to 250° C., are preferred from an industrial point of view.

The apparatus 10 further includes an amine tank 13 for storing 1,8-diazabicyclo[5.4.0]undec-7-ene (liquid, hereafter also referred to as DBU), an example of an amine that easily forms a complex with a specific fullerene (especially higher fullerenes).

The amines include, besides DBU, any compound having two or more nitrogen atoms and capable of forming a complex with a specific fullerene, for example, a compound having an amidine structure with a substructure where two nitrogen atoms are bonded through one atom represented by the formula (1), or a cyclic amidine structure represented by the formula (2). Examples of the amines are such as 1,5-diazabicyclo[4.3.0]non-5-ene, 1,1,3,3-tetramethylguanidine, 2-methyl-2-imidazoline, 1,2-dimethyl-1,4,5,6-tetrahydropyrimidine, 1-methyl-2-imidazoline, 2-alkylamidine, guanidine, tetrakis(dimethylamino)ethylene, and 1-alkyl-1,2,3-triazoline.

The apparatus 10 includes a first mixing tank 14 in which the fullerene mixture and the DBU are mixed in the TMB to form a first complex of the higher fullerenes contained in the fullerene mixture with the DBU. The first mixing tank 14 is provided with a temperature controller (not shown) capable of adjusting the temperature inside the first mixing tank 14 in a range of −50 to 100° C. and an agitating blade for efficiently mixing the fullerene mixture with the DBU. The pressure in the first mixing tank 14 during the mixing is not specifically limited and the mixing is carried out at normal pressures.

While the agitating blade of the first mixing tank 14 is rotated at an appropriate speed, the DBU is gradually supplied from the amine tank 13 by dripping. A temperature preferable for the dripping is, e.g., −50 to 100° C. Especially a temperature of −20 to 50° C. accelerates production speed of the complex, and is thus preferable. Amount of the drip depends on a fullerene content to be separated, but in general, the amount is preferably 2 to 50 molar equivalents of fullerenes to be separated. After completion of the dripping, it is preferable to stir the resultant solution until the complex is formed sufficiently.

In the first mixing tank 14, mainly the higher fullerenes contained in the fullerene mixture and the DBU form the first complex represented by a formula (4).

$$\text{Higher fullerene} \cdot (\text{DBU})_n \qquad (4)$$

(n=1−2)

The produced first complex forms a precipitate in the TMB, thus the first complex can be separated using a method such as filtration or decantation. C60, C70 and DBU not forming the complex are dissolved in the TMB. C60 and C70 also form complexes with the DBU and form precipitates although the amounts thereof are little.

(Second Process)

The apparatus 10 includes a separator, e.g. a first continuous pressure filter 15, for separating the first complex from a solution (first solution) in which the C60 and the C70 are dissolved. The separator may be, besides the pressure filter, a vacuum filter or a centrifuge (the same for separators described hereafter). The apparatus 10 includes a first dissociation tank 16 where the first complex separated by the first filter 15 is dissociated into the higher fullerenes and the amine. The first dissociation tank 16 is provided with an agitating blade for efficiently mixing the first complex with trifluoroacetic acid, and a temperature controller not shown.

The apparatus 10 has an acid tank 17 for storing an acid, e.g., trifluoroacetic acid that is an organic acid. The first complex separated by the first filter 15 and the TMB in the solvent tank 12 are supplied into the first dissociation tank 16 to suspend the first complex in the TMB, and then the trifluoroacetic acid is further supplied from the acid tank 17. In the first dissociation tank 16, the first complex and the trifluoroacetic acid are mixed. Since trifluoroacetic acid has stronger interaction with DBU than with higher fullerenes, the first complex is dissociated into higher fullerenes dissolved in the TMB and a salt of the DBU with the trifluoroacetic acid, and the generated salt is precipitated.

The apparatus 10 further includes a separator, e.g. a second continuous pressure filter 18, for separating a solution of the higher fullerenes from the salt of the DBU with the trifluoroacetic acid. The apparatus 10 has a first conical ribbon mixer dryer 19. To the first conical ribbon mixer dryer 19, the solution of the higher fullerenes separated by the second filter 18 is supplied, and the solution is dried at a temperature equal to or higher than the boiling point of TMB, e.g. 130° C., and at a pressure of 0.3 kPa until the TMB is removed thoroughly (e.g., for 25 hours) to obtain solid higher fullerenes. The removed TMB is supplied into the solvent tank 12 for reuse. Although the first conical ribbon mixer dryer 19 is used for removal of the TMB from the solution of the higher fullerenes, a tray vacuum dryer, a conical dryer or the like may be used (the same for conical ribbon mixer dryers described hereunder).

Here, when the solution of the higher fullerenes separated by the second filter 18 contains an excessive amount of the amine that does not form a complex with the higher fullerenes, it is preferable to remove the amine prior to the removal of the TMB by the first conical ribbon mixer dryer 19. The amine may be removed, for example, by adding an organic acid to the solution to precipitate the amine as a salt with the acid, or by mixing the solution with an acid aqueous solution or water to remove the amine into a water layer (hereafter, also the same as to the separation of the C60 and the C70).

The solution from which the amine has been removed can be used as it is in a subsequent reaction, or the higher fullerenes can be extracted as a solid by a method such as crystallization, sublimation, or a combination of these methods besides solvent elimination (hereunder, also the same for C60 and C70).

(Third Process)

The apparatus 10 includes a second mixing tank 20 where the C70 contained in the TMB separated by the first filter 15 is made to react with DBU to form a second complex. In the TMB separated by the filter 15, C60 and C70 are dissolved. The second mixing tank 20 is provided with a temperature controller (not shown) capable of adjusting the temperature inside the second mixing tank 20 in a range of −50 to 100° C. and an agitating blade for efficiently mixing the C60 and the C70 with the DBU. The pressure in the second mixing tank 20 during the mixing is not specifically limited and the mixing is carried out at normal pressures.

While the agitating blade of the second mixing tank 20 is rotated at a proper speed, the DBU is supplied by being gradually dripped from the amine tank 13. The temperature in the second mixing tank 20 and the dripping speed of the amine are the same as those at the time of forming the first complex in the first mixing tank 14.

In the second mixing tank 20, mainly the C70 and the DBU form the second complex represented by a formula (5).

$$\text{C70} \cdot (\text{DBU})_n \qquad (5)$$

(n=1−2)

The produced second complex forms a precipitate in the TMB, thus the second complex can be separated using a method such as filtration or decantation. C60 and DBU not forming the complex are dissolved in the TMB. C60 also forms a complex with the DBU and forms a precipitate although the amount thereof is little.

(Fourth Process)

The apparatus 10 includes a separator, e.g. a third continuous pressure filter 21, for separating the second complex from a solution (a second solution) in which the C60 is dissolved. The apparatus 10 further includes a second dissociation tank 22 where the second complex separated by the third filter 21 is dissociated into the C70 and the amine. The second dissociation tank 22 is provided with an agitating blade for efficiently mixing the second complex with trifluoroacetic acid supplied from the acid tank 17 and a temperature controller not shown.

The second complex separated by the third filter 21 and the TMB in the solvent tank 12 are supplied into the second dissociation tank 22, the second complex is suspended in the TMB, and subsequently trifluoroacetic acid is supplied from the acid tank 17 to the tank 22. In the second dissociation tank 22, the second complex and the trifluoroacetic acid are mixed. Since trifluoroacetic acid has stronger interaction with DBU than with C70, the second complex is dissociated into C70 dissolved in the TMB and a salt of the DBU with the trifluoroacetic acid, and the generated salt is precipitated.

The apparatus 10 has a separator, e.g. a fourth continuous pressure filter 23, for separating a solution of C70 from the salt of the DBU and the trifluoroacetic acid. The apparatus 10 also has a second conical ribbon mixer dryer 24. To the second conical ribbon mixer dryer 24, the solution of C70 separated by the fourth filter 23 is supplied, and the solution is dried at a temperature equal to or higher than the boiling point of TMB, e.g. 130° C., and at a pressure of 0.3 kPa until the TMB is removed thoroughly (e.g., for 25 hours) to obtain solid C70. The removed TMB is supplied into the solvent tank 12 for reuse.

The apparatus 10 includes a third conical ribbon mixer dryer 25. In the third conical ribbon mixer dryer 25, a solution of C60 separated by the third filter 21 is dried at a temperature equal to or higher than the boiling point of TMB, e.g. 130° C., and at a pressure of 0.3 kPa until the TMB is removed thoroughly (e.g. for 25 hours) to obtain a solid of C60. The removed TMB is supplied to the solvent tank 12 for reuse.

By the above-described procedures, the specific fullerene(s) can be obtained at high purity. However, repeating the procedures entirely or partly for multiple times is effective for further enhancement of the purity. Moreover, a combination of the procedures and any one or more of techniques such as chromatography, crystallization, sublimation, and inclusion (complex formation), which are conventional methods of fullerene separation, is also effective to enhance the purity of the fullerenes.

(Experiment 1: Separation of C60, C70 and Higher Fullerenes from the Fullerene Mixture Using DBU)

A fullerene mixture in an amount of 0.56 g (having a composition of C60: 64 wt. %, C70: 23 wt. %, higher fullerenes: 13 wt. %, the same hereunder) was dissolved in 19.4 g of TMB, and this solution was cooled to 0° C. Here, 0.56 g of the fullerene mixture contains 0.36 g of C60, 0.13 g of C70, and 0.07 g of higher fullerenes. Subsequently, 0.20 g of DBU was gradually added taking one minute. The solution was stirred for 1.5 hours, whereby a precipitate having a sedimentation property, i.e., the first complex, was formed.

The solution was filtrated to obtain the first complex and the first solution. The first complex was suspended in 100 g of TMB and 0.50 g of trifuluoroacetic acid was added thereto. This solution was heated to 40° C. and stirred for 2 hours, whereby the higher fullerenes and a precipitate of a salt of the DBU with the trifluoroacetic acid were obtained. The precipitate was separated by filtration. The obtained filtrate was washed with 10.0 g of demineralized water (ion-exchange water) until the wash water was neutral (e.g., washed for three times).

After the washing, the solution was analyzed with HPLC, and 0.003 g of fullerenes mainly comprising the higher fullerenes was obtained. The obtained TMB solution contained 60 wt. % higher fullerenes, and the recovery rate of higher fullerenes from the fullerene mixture was 3 wt. %. Furthermore, solid higher fullerenes can be obtained by removing TMB from the TMB solution of the higher fullerenes.

The obtained first solution was kept at 0° C., and 0.40 g of DBU was gradually added thereto taking one minute. This solution was stirred for one hour, whereby a precipitate having a sedimentation property, i.e., the second complex, was formed. This solution was filtrated to obtain the second complex and the second solution.

The second complex was suspended in 100 g of TMB and 0.05 g of trifuluoroacetic acid was added thereto. This solution was heated to 40° C. and stirred for 2 hours, whereby C70 and a precipitate of a salt of the DBU and the trifluoroacetic acid were obtained. The precipitate was separated by filtration. The obtained filtrate was washed with 10.0 g of demineralized water until the wash water was neutral (e.g., washed for three times).

After the washing, this solution was analyzed with HPLC, and 0.009 g of fullerenes mainly comprising C70 was obtained. This obtained TMB solution contained 64 wt. % C70, and the recovery rate of C70 from the fullerene mixture was 4 wt. %. Furthermore, solid C70 can be obtained by removing TMB from the TMB solution of C70.

The second solution was washed with 10.0 g of demineralized water until the wash water was neutral (e.g., washed for three times). After the washing, this TMB solution was analyzed with HPLC, and 0.27 g of fullerenes mainly comprising C60 was obtained. The obtained TMB solution contained 99 wt. % C60, and the recovery rate of C60 from the fullerene mixture was 74 wt. %. Furthermore, solid C60 can be obtained by removing TMB from the TMB solution of C60.

(Experiment 2: Separation of C60 from the Fullerene Mixture Using DBN)

A fullerene mixture (0.34 g) was dissolved in 19.7 g of TMB, and this solution was cooled to 0° C. Here, 0.34 g of the fullerene mixture contained 0.22 g of C60, 0.08 g of C70, and 0.04 g of higher fullerenes. Subsequently, 0.28 g of DBN was gradually added taking one minute. This solution was stirred for 5 hours, whereby a complex having a sedimentation property was obtained, and the complex was separated by filtration. This filtrate was washed with 20.0 g of demineralized water until the wash water was neutral (e.g., washed for three times). After the washing, this TMB solution was analyzed with HPLC, and 0.18 g of fullerenes mainly comprising C60 was obtained. This obtained TMB solution contained 96 wt. % C60, and the recovery rate of C60 from the fullerene mixture was 82 wt. %. Furthermore, solid C60 can be obtained by removing TMB from the TMB solution of C60;

(Experiment 3: Separation of C60 from the Fullerene Mixture Using IDN)

A fullerene mixture (0.34 g) was dissolved in 19.7 g of TMB, and this solution was cooled to 0° C. Subsequently, 0.30 g of IDN was added gradually taking one minute. This solution was stirred for 3 hours, whereby a complex having a sedimentation property was formed, and the complex was separated by filtration. This filtrate was washed with 20.0 g of demineralized water until the wash water was neutral (e.g., washed for three times.) After the washing, this TMB solution was analyzed with HPLC, and 0.13 g of fullerenes mainly comprising C60 was obtained. This obtained TMB solution contained 69 wt. % C60, and the recovery rate of C60 from the fullerene mixture was 60 wt. %. Furthermore, solid C60 can be obtained by removing TMB from the TMB solution of C60.

(Experiment 4: Separation of C60 from the Fullerene Mixture Using TMG)

A fullerene mixture (0.34 g) was dissolved in 19.7 g of TMB, and this solution was cooled to 0° C. Subsequently, 0.26 g of TMG was added gradually taking one minute. This solution was stirred for 5 hours, whereby a complex having a sedimentation property was formed, and the complex was separated by filtration. This filtrate was washed with 20.0 g of demineralized water until the wash water was neutral (e.g., washed for three times). After the washing, this TMB solution was analyzed with HPLC, and 0.21 g of fullerenes mainly comprising C60 was obtained. This obtained TMB solution contained 69 wt. % C60, and the recovery rate of C60 from the fullerene mixture was 96 wt. %. Furthermore, solid C60 can be obtained by removing TMB from the TMB solution of C60.

(Experiment 5: Complex of C70 with DBU)

C70 (0.05 g) was dissolved in 3.0 g of TMB, and this TMB solution was cooled to 0° C. Subsequently, 0.05 g of DBU was added gradually taking one minute. This TMB solution was stirred for 5 hours, whereby a complex was formed. After the TMB solution was separated by filtration, the filtered residual was vacuum dried, and 0.03 g of the complex of the C70 and the DBU in a solid state was obtained. By elemental analysis, the solid complex contained 86.3 wt. % of C; 2.0 wt. % of H; and 2.8 wt. % of N. Here, calculated from the ratio of C to N, the number of DBU attached to C70 was 1.1.

(Experiment 6: Complex of C60 with DBU)

C60 (0.05 g) was dissolved in 3.0 g of TMB, and this TMB solution was cooled to 0° C. Subsequently, 0.05 g of DBU was added gradually taking one minute. This TMB solution was stirred for 5 hours, whereby a complex was formed. The TMB solution was separated by filtration, and then the filtered residual was vacuum dried, whereby 0.02 g of complex of the C60 and the DBU in a solid state was obtained. By elemental analysis, the solid complex contained: 84.1 wt. % of C; 2.8 wt. % of H; and 4.4 wt. % of N. Here, calculated from the ratio of C to N, the number of DBU attached to C60 was 1.7.

The present invention is not limited to the above-described embodiment or experiments, and various modifications may be made without departing from the scope or sprit of the present invention. For instance, the present invention includes a case where the method of fullerene separation and the complex comprising a fullerene according to the present invention comprise a part of or all of the above respective embodiments and experiments.

For instance, in the method of fullerene separation of the above embodiment, when the complex of the fullerene and the amine is soluble in the solvent, i.e., when the complex does not form a precipitate, crystallization or the like may be employed to separate the complex from fullerenes not forming the complex.

INDUSTRIAL APPLICABILITY

In the method of fullerene separation and the complex of the fullerene according to the present invention, a complex is formed by a specific fullerene in the fullerene mixture comprising any two or more of C60, C70 and higher fullerenes having greater than 70 carbon atoms with the amine having two or more nitrogen atoms, and the complex is separated from a solution in which fullerenes not forming the complex are dissolved. Accordingly, the specific fullerene and the fullerenes not forming the complex can be separated from the fullerene mixture. Thereby, the specific fullerene can be easily separated at low cost and less expensive fullerenes can be provided.

The invention claimed is:

1. A method of fullerene separation comprising the steps of:
   bringing a fullerene mixture into contact with an amine A in a solvent to form an amine complex of a specific fullerene contained in the fullerene mixture with the amine A, the fullerene mixture comprising any two or more of C60, C70 and higher fullerenes having greater than 70 carbon atoms, the amine A having two or more nitrogen atoms, the amine complex being insoluble in the solvent; and
   separating the complex from a solution in which fullerenes not forming the complex are dissolved
   wherein the separation step is not achieved by chromatography.

2. The method of fullerene separation according to claim 1, wherein the complex is dissociated into the specific fullerene and the amine A to obtain the specific fullerene.

3. The method of fullerene separation according to claim 2, wherein the dissociation of the complex is carried out by bringing the complex into contact with an acid.

4. The method of fullerene separation according to claim 1, wherein the amine A has a substructure in which the two nitrogen atoms are bonded through one atom.

5. The method of fullerene separation according to claim 4, wherein the amine A having the substructure in which the two nitrogen atoms are bonded has an amidine structure represented by a formula (1).

6. The method of fullerene separation according to claim 5, wherein the amine A having the amidine structure has a cyclic amidine structure represented by a formula (2)

(n is an integer of 2 or more.).

7. The method of fullerene separation according to claim 6, wherein the amine A having the cyclic amidine structure is any one of 1,8-diazabicyclo[5.4.0]undec-7-ene and 1,5-diazabicyclo[4.3.0]non-5-ene.

8. The method of fullerene separation according to claim 1, wherein the fullerene mixture comprises C60, C70 and higher fullerenes having greater than 70 carbon atoms, the amine A is an amine B to form an amine complex with the higher fullerene, the complex is a first complex formed by the amine B and the higher fullerene, the solution is a first solution in which the C60 and the C70 are dissolved; and the first solution is brought into contact with an amine C having two or more nitrogen atoms to obtain a second amine complex formed by the C70 and the amine C; and then the second complex is separated from a second solution in which the C60 is dissolved.

9. The method of fullerene separation according to claim 8, wherein the first and the second complexes are insoluble in the solvent.

10. The method of fullerene separation according to claim 9, wherein the first complex is dissociated into the higher fullerenes and the amine B to obtain the higher fullerenes.

11. The method of fullerene separation according to claim 10, wherein the dissociation of the first complex is carried out by bringing the first complex into contact with an acid.

12. The method of fullerene separation according to claim 9, wherein the second complex is dissociated into the C70 and the amine C to obtain the C70.

13. The method of fullerene separation according to claim 12, wherein the dissociation of the second complex is carried out by bringing the second complex into contact with an acid.

14. The method of fullerene separation according to claim 8, wherein each of the amines B and C has a substructure in which the two nitrogen atoms are bonded through one atom.

15. The method of fullerene separation according to claim 14, wherein each of the amines B and C having the substructure in which the two nitrogen atoms are bonded has an amidine structure represented by a formula (1).

(1)

16. The method of fullerene separation according to claim 15, wherein each of the amines B and C having the amidine structure has a cyclic amidine structure represented by a formula (2)

(2)

(n is an integer of 2 or more.).

* * * * *